(12) United States Patent
Hospodor

(10) Patent No.: US 8,980,941 B2
(45) Date of Patent: Mar. 17, 2015

(54) **CONTROLLED *CANNABIS* DECARBOXYLATION**

(76) Inventor: Andrew David Hospodor, Santa Cruz, CA (US)

( * ) Notice: Subject to any disclaimer, the term of this patent is extended or adjusted under 35 U.S.C. 154(b) by 729 days.

(21) Appl. No.: 13/199,123

(22) Filed: Aug. 19, 2011

(65) Prior Publication Data
US 2012/0046352 A1    Feb. 23, 2012

Related U.S. Application Data

(60) Provisional application No. 61/401,824, filed on Aug. 19, 2010.

(51) Int. Cl.
| | |
|---|---|
| *A61K 31/352* | (2006.01) |
| *A23L 1/30* | (2006.01) |
| *A61K 36/00* | (2006.01) |
| *A61K 31/35* | (2006.01) |
| *A23G 1/42* | (2006.01) |
| *A23G 1/48* | (2006.01) |
| *A61K 9/00* | (2006.01) |
| *B65D 73/00* | (2006.01) |
| *B65D 75/36* | (2006.01) |
| *A61K 9/06* | (2006.01) |

(52) U.S. Cl.
CPC . *A61K 31/35* (2013.01); *A23G 1/42* (2013.01); *A23G 1/48* (2013.01); *A23L 1/3002* (2013.01); *A61K 9/0053* (2013.01); *A61K 31/352* (2013.01); *B65D 73/0092* (2013.01); *B65D 75/367* (2013.01); *A61K 9/06* (2013.01); *B65D 2575/367* (2013.01)
USPC .............. 514/454; 424/725; 424/774; 426/72

(58) Field of Classification Search
None
See application file for complete search history.

(56) References Cited

U.S. PATENT DOCUMENTS

| | | | |
|---|---|---|---|
| 2005/0042172 A1* | 2/2005 | Whittle | 424/46 |
| 2006/0068034 A1* | 3/2006 | Whittle | 424/725 |
| 2006/0134181 A1 | 6/2006 | Altaffer et al. | |
| 2006/0160888 A1 | 7/2006 | Kottayil et al. | |
| 2008/0102132 A2 | 5/2008 | Giner et al. | |

OTHER PUBLICATIONS

Whiteley, "Cofactor requirements for the decarboxylation of succinate", Communications to the Editor, vol. 75, pp. 1518-1519 (Mar. 20, 1953).*

"Cofactor", the Free Dictionary, pp. 1-2, [online], [retrieved on Apr. 21, 2014]. <URL: http://www.thefreedictionary.com/cofactor.*

(Continued)

*Primary Examiner* — Ernst V Arnold
*Assistant Examiner* — Kyung Sook Chang
(74) *Attorney, Agent, or Firm* — Robert J. Rapp

(57) ABSTRACT

The invention is a process for the controlled decarboxylation of *cannabis* wherein Medicinal Delta-9 tetrahydrocannabinol ($\Delta^9$-THC) and other cannabinoid medicinal substances are decarboxylated through a chemical reaction facilitated by a cofactor. The amount of medicinal *cannabis* decarboxylated will be directly proportional to the amount of cofactor used. Use a small amount of the cofactor and only some of the medicinal *cannabis* contained in raw *cannabis* will be converted from an acidic form into a non-acidic form. Use a large amount of the cofactor and most or all of the medicinal *cannabis* will be decarboxylated. The reaction is proportional to the molar mass of cofactor.

5 Claims, 2 Drawing Sheets

Controlled Decarboxylation Process

(56) References Cited

OTHER PUBLICATIONS

Medical Cannabis Dispensary (MCD) Regulations for Preparation of Edible Cannabis Products. City and County of San Francisco Department of Public Health Jun. 18, 2009.
Commentary Medial Marijuana by Jane B Marmor MD. Redwood City CA. Jun. 1998.
Medicinal Cannabis Edibles, Denver Relief Denver CA. 2009.
Oregon Medical Marijuana Program, Cannabis Recipes, (last visit Feb. 7, 2013).
Medical Marijuana in WA Patients and defenders; Jun. 17, 2009 Federal Way Mirror by Andy Hobbs.
Chemical ecology of Cannabis, David W. Pate, Journal of the International Hemp Association Postbus 75007; 1070 AA Amsterdam, The Netherlands; 1994.

* cited by examiner

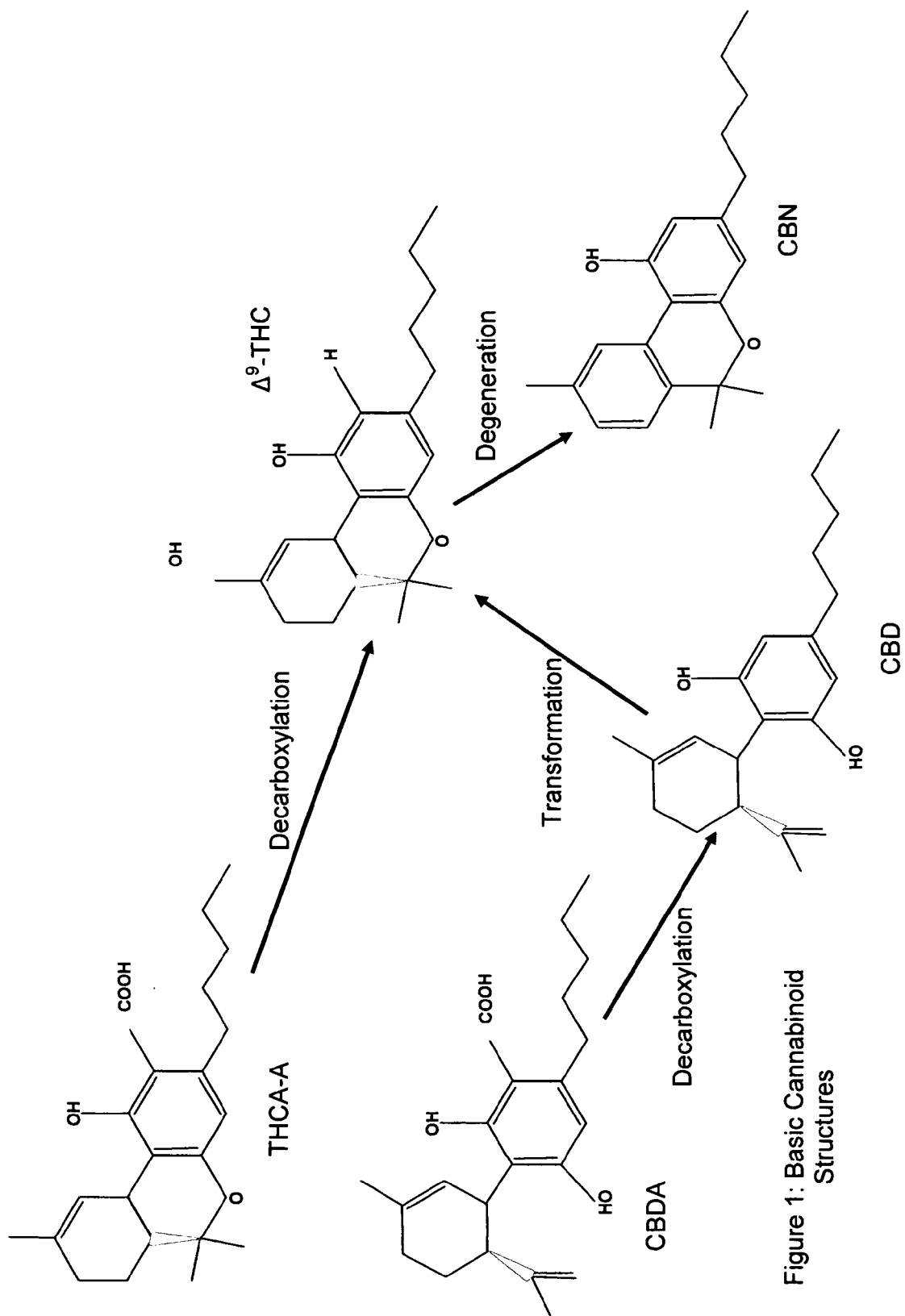
Figure 1: Basic Cannabinoid Structures

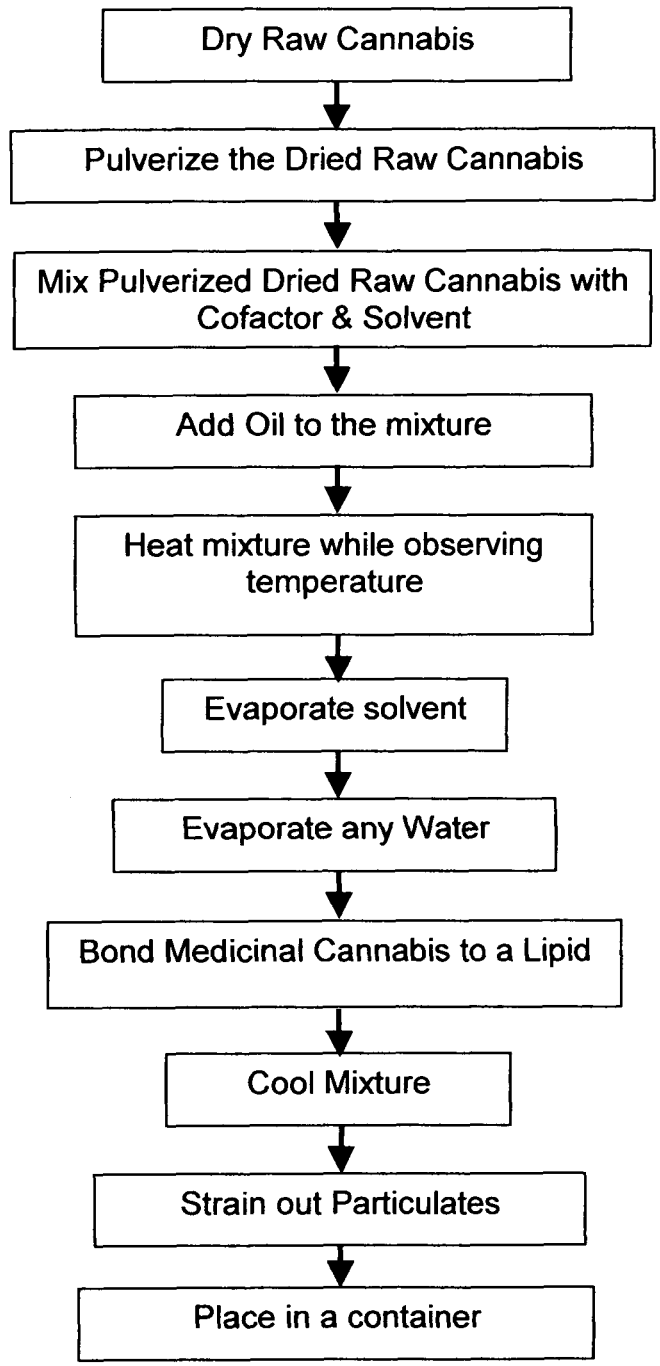
Figure 2: Controlled Decarboxylation Process

CONTROLLED CANNABIS DECARBOXYLATION

CROSS REFERENCE TO RELATED APPLICATIONS

This application claims benefit of Provisional Patent Application No. 61/401,824 Medicinal *Cannabis* in a Fatty Foodstuff filed Aug. 19, 2010

FEDERAL SUPPORT STATEMENT

Not Applicable

SEQUENCE LISTING

Not Applicable

BACKGROUND OF THE INVENTION

Raw *cannabis* contains tetrahydrocannabinol carboxylic acid (THC-COOH); this substance is also referred to as THC acid, Δ9-THC acid, THCA-A, or THCA.

The article that appears in the Journal of Chromatography "Innovative development and validation of an HPLC/DAD method for the qualitative determination of major cannabinoids in *cannabis* plant material" reference [1], see section 1.1; this article reports that THC-B is another form of THC acid that appears only in trace amounts in raw *cannabis*. This article also reports other substances in raw *cannabis*, including cannabidiolic acid (CBDA) and cannabigerolic acid (CBGA); a substance cannabinol (CBN) is also reported present in aged *cannabis*.

THC acid may be converted into the psychoactive substance Tetrahydrocannabinol (THC), also known as ($\Delta^9$-THC) through processes that decarboxylate the THC acid. Decarboxylation is a chemical reaction that converts an acid to a phenol and releases carbon-dioxide ($CO_2$); a carbon atom is removed from a carbon chain.

Reference [1] also discusses and shows the decarboxylation of THC acid into $\Delta^9$-THC, the decarboxylation of cannabidiolic acid (CBDA) into cannibidiol (CBD), and the decarboxylation of cannabigerolic acid (CBGA) into cannabigerol (CBG). Decarboxylation occurs when *cannabis* is exposed to heat, light, cofactors or solvents.

Historical and anecdotal reports of the medicinal use of *cannabis* date back for millennia, in recent decades the psychoactive ingredient Δ9-THC has been extracted through a verity of processes; to date processes that decarboxylate of THCA-A into psychoactive $\Delta^9$-THC in controlled ways use toxic solvents; frequently a distillation process such as fractal distillation is then used to separate the toxic solvents from the active ingredient after decarboxylation.

THCA-A decarboxylated into $\Delta^9$-THC in controlled ways using toxic solvents:

Related U.S. Pat. Nos. 6,365,416 B1 [2], 6,730,519 [3]; and patent publication US 2002/0039795 A1 [4] by Elsohly et. al. isolates $\Delta^9$-THC from *cannabis* base material using toxic non-polar organic solvents such as hexane, heptane, or iso-octane. U.S. Pat. No. 6,730,519 [3] was sponsored by a National Institute for Drug Abuse, Small Business Innovative Research grant; Related U.S. Pat. Nos. 6,365,416 [2] and 6,730,519 [3] in their Background of the Invention section provide excellent details regarding the medical use of $\Delta^9$-THC. the inventors conclude that extracting $\Delta^9$-THC from raw *cannabis* material is more cost effective than synthetically created FDA approved medicinal THC, and they reference prior art dating from 1942 through 1972 that relate to THC extraction or analysis of hashish and "red oil"; the processes referenced frequently use toxic elements such as carbon tetrachloride, benzene, N-dimethyl formamide/cyclohexane, or hexane.

U.S. Pat. Nos. 7,524,881 B2 [5], and 7,592,468 B2 [6] Goodwin et. Al. discloses processes that extract $\Delta^9$-THC from raw *cannabis*; this process converts THC acid into salt using non-polar solvents such as pentane, hexane, heptane, or octane; again toxic solvents are used.

GW pharmaceuticals of Great Britain has created a vaporized form of medicinal $\Delta^9$-THC called Savitex.

Savitex is administered with an inhaler, similar to an inhaler used to administer asthma medication. Information regarding the therapeutic use and mechanisms of action of Savitex can be found on GW pharmaceuticals website. Savitex is currently being studied for affectivity by patients with multiple sclerosis, cancer pain, and neuropathic pain.

GW pharmaceutical reports that the human body has receptors to frequently called CB1 and CB2 and that Δ9-THCbonds to CB1 receptors located in the human brain, where cannabinoids bond to CB2 receptors located in the human lymphatic system. The URLs below link to reports on GW Pharmaceuticals website, they describe that Savitex is being used medicinally and describe some of the mechanisms of action of medicinal *cannabis*; these reports have also been combined into reference [7]:

http://www.gwpharm.com/multiple-sclerosis.aspx
http://www.gwpharm.com/cancer-pain.aspx
http://www.gwpharm.com/neuropathic-pain.aspx
http://www.gwpharm.com/mechansims-action.aspx The science related to how these various substances affects the human body is in its infancy, even so GW pharmaceuticals of Great Britain reports that the human body has receptors CB1 and CB2 to which $\Delta^9$-THC and CBD (cannabidiol) bond respectively. They also report that the human body has CB1 receptors predominately located in the human brain, and CB2 receptors located predominantly in the human lymphatic system.

Most reports indicate that psychoactive substance $\Delta^9$-THC is the primary active medicinal substance derived from *cannabis*; other substances contained within *cannabis* may however also have medicinal qualities. Some researchers suspect that cannabidiol (CBD) may mitigate pain; more scientific research is needed to understand how the various substances derived from *cannabis* affect the human body. GW Pharmaceuticals also state in their Mechanisms of Action "The combination of THC, CBD and essential oils in *cannabis*-based medicinal extracts may produce a therapeutic preparation whose benefits are greater than the sum of its parts".

Reference [8] "Effects of canabidiol on schizophrenia-like symptoms in people who use *cannabis*"; from The British Journal of Psychiatry (2008) reports that $\Delta^9$-THC tends to "elevate levels of anxiety and psychotic symptoms in healthy individuals. In contrast, cannabidiol (CBD), another major constituent of some strains of *cannabis*, has been found to be anxiolytic and to have antipsychotic properties, and may be neuroprotective in humans".

A key finding of this study [8]: "The TCH only group showed higher levels of positive schizophrenia-like symptoms compared with the no cannabinoid and the TCH+CBD groups . . . . This provides evidence of the divergent properties of cannabinoids and has important implications for research into the link between *cannabis* use and psychosis".

Reference [9] Therapeutic Potential of Non-Psychotropic Cannabidiol in Ischemic Stroke; Hayakawa, Mishima, &

Fujiwara; Dept. of Neuopharmacology, Faculty of Pharmaceutical Sciences, Fukuoka University, Published Jul. 8, 2010. $\Delta^9$-THC. This reference reviews various substances found within *cannabis*, it states in its introduction that "*Cannabis* contains over 60 different terpeno-phenol compounds that have been identified so far but the role and importance of many of these has yet to be fully understood".

Reference [9] also states "cannabidiol (CBD), cannabigerol (CBG), cannabidvarin (CBDV) are known as non-psychoactive components of *cannabis*. These compounds have shown anti-inflammatory, immunosuppressive, analgesic, anxiolytic and anti-cancer effects". This reference also discusses the neuroprotective abilities of CBD in stroke victims.

The above mentioned references [7]. [8], and [9] demonstrate that $\Delta^9$-THC is not the only substance contained within medicinal *cannabis* with therapeutic benefits to people. All of these references recommend additional study or mention that the effect of the substances contained within *cannabis* on humans is not fully understood. Variations of ratios of substances contained within medicinal *cannabis* are reported to have different effects; as in reference [8], adjusting the ratio $\Delta^9$-THC to CBD is shown to be critical in limiting anxiety and psychotic symptoms associated with the intake of high concentrations of $\Delta^9$-THC as compared to CBD. New substances and therapeutic uses of substances derived from *cannabis* are likely to be discovered as research in this field continues.

Reference [10] "Isolation of $\Delta^9$-THCA-A from hemp and analytical aspects concerning the determination of $\Delta^9$-THC in *cannabis* products"; Dussy, et al. Institute of Legal Medicine, Basel Switzerland, available online Aug. 18, 2004. This reference quantifies the amount of THC acid (THCA-A) that is converted into $\Delta^9$-THC when *cannabis* is smoked under various conditions: Section 2 reviews *cannabis* reduced into a concentrated THC acid (THCA-A) solution using solvents. Samples of the concentrate are then decarboxylated at various temperatures in a Gas Chromatography (GC) oven; some samples are then analyzed using High Performance Liquid Chromatography (HPLC). FIG. 3 in this disclosure shows:

Partial decarboxylation of concentrated THCA-A in solution into $\Delta^9$-THC at 120 degrees C.

Significant decarboxylation of concentrated THCA-A in solution into $\Delta^9$-THC at 140 degrees C.

Nearly complete decarboxylation of concentrated THCA-A in solution into $\Delta^9$-THC at 160 degrees C. along with some degradation of $\Delta^9$-THC into cannabinol and dihydrocannabinol at 160 degrees C.

A significant percentage of $\Delta^9$-THC being degraded into cannabinol and dihydrocannabinol at 180 degrees C.

The decarboxylation of concentrated THCA-A in solution into $\Delta^9$-THC, and the degradation of $\Delta^9$-THC into cannabinol and dihydrocannabinol are shown to vary with temperature. Temperature controls are therefore one mechanism for controlling ratios of certain substances in medicinal *cannabis*.

Note: An embodiment of the invention described later in this document uses temperature and other mechanisms to control the decarboxylation of THCA-A in raw *cannabis*.

Concentration ratios of THC acid (THCA-A) to cannabidiolic acid (CBDA) vary with the types *cannabis* selected; THCA-A decarboxylates into $\Delta^9$-THC, and CBDA decarboxylates into CBD.

Reference [11] is an example of *cannabis* related material available to the general public Wikipedia under "Cannabiniod" in August 2010. Many of the same substances discussed in previous references are also reviewed in reference [11].

Reference [12] *Cannabis* and *Cannabis* Extracts: Greater Than the sum of Their Parts?, by John M. McPartland and Ethan B. Russo; 2001 The Haworth Press, Inc. this reference reports the boiling temperature of *cannabis* related substances, the boiling temperatures reported include: $\Delta$9-THC 157 degrees C., cannabidiol (CBD) 160-180 degrees C., cannabinol (CBN) 185 degrees C., and $\Delta$8-THC 175-178 degrees C.

Reference [13] U.S. Pat. No. 7,674,922 "Process for Production of Delta-9-Tetrandrocannabinol", Burdick et al. Granted Mar. 9, 2010. This reference produces $\Delta$9-THC using "ortanoaluminum-based Lewis acid catalyst", a metallic based catalyst.

Reference [14] a drawing from www.*Cannabis*-Science.com showing chemical structures in *cannabis* related materials. The drawing is entitled "Cannabinoids"; the drawing shows an important aspect of cannabinoid science, Cannabidiol (CBD) can be converted into $\Delta$9-THC. The chemical structures are very similar, they have the same molecular weight and the same chemical formula. Reference [15] patent application publication US 2008/0221339 by Webster et al. published Sep. 11, 2008 discusses the conversion of Cannabidiol (CBD) to $\Delta$9-THC and $\Delta$8-THC are discussed in; various toxic solvents are used in these processes; one *cannabis* related substance is converted another through a chemical process.

Reference [16] Hemp Husbandry, an excerpt from Chapter 6 Cannabinoid Chemistry: Robert A. Nelson, Copyright 2000; another excellent review of the chemistry of *cannabis* Uncontrolled Crude Processes:

Other processes have been used to extract $\Delta$9-THC from raw *cannabis* in uncontrolled ways, some of these processes use toxic materials and others do not; frequently such processes attempt to produce a final product in a single uncontrolled crude step.

Examples of such processes include the use of butane, a toxic solvent, to make the *cannabis* "red oil" commonly called hash oil. A method found on the internet reference [17] "How To Make Hash Oil from Marijuana" reviews the use of butane, here raw *cannabis* is saturated in butane, the butane reduces the raw *cannabis* into an oil that is separated from the plant material, the butane evaporates continuously during the process of reduction; a paper filter is used to separate the oil from plant material. The author also recommends a secondary process of mixing the oil with isopropyl alcohol, then evaporating the isopropyl alcohol overnight by letting it sit. The author of this reference believes that the isopropyl alcohol reduces the photosensitivity of THC contained within the oil. The process disclosed has no scientific controls, and shows disregard for laws relating to treating *cannabis* as a controlled substance or preparation of food products. The disclosure is provided as an example of uncontrolled methods that are available to the public.

In contrast, uncontrolled crude processes that use no toxic chemicals include simply baking *cannabis* into cookies or bread, or making a tea by steeping *cannabis* in hot water. *Cannabis* infused dairy butter can be made by melting dairy butter in a pot, adding raw *cannabis* and cooking the mixture for a period of time, up to 24 hours.

Hashish may be made without the use of toxic chemicals, "How to Made Wicked Hash" by Lisa Scammel and Bianca Sind [17] reviews various methods for separating THC acid infused trichomes from *cannabis* plant materials, forming it into blocks that are then covered in paper, and then heated in fry pan until the blocks melt; the processes reviewed are uncontrolled, and have no scientific controls, they include: "Flat Screening", "Drum Machines", "the blender method", and "ice-water filtration" methods are reviewed. This reference is also provided as another example of uncontrolled crude methods that are available to the public. This disclosure also shows some disdain for laws relating to *cannabis* as a controlled substance.

Smoking, in the form of a cigarette or pipe, is the most frequently used uncontrolled process for decarboxylating *cannabis*.

The processes discussed above that rely on temperature simply use temperature yet do not control temperature; if the temperature is too low decarboxylation will be incomplete, if temperatures are too high decarboxylated substances within *cannabis* will be lost to evaporation. Temperature control is therefore characteristic of a process that relies on temperature to decarboxylate. This is why the "uncontrolled" processes reviewed above that rely on temperature are truly uncontrolled.

Processes discussed above that use toxic solvents in "uncontrolled" ways rely on saturating available *cannabis* with the toxic solvent then filtering oil from plant parts.

The process sprays a solvent through a tube filled with a volume of *cannabis* as described in reference [18] implies that more or less solvent will be required will be required to remove all of the trichombes from available *cannabis*; even small variables, such as how the *cannabis* is prepared will affect the efficiency of the solvent's ability to reduce the *cannabis* uniformly.

For example as the raw *cannabis* material density varies per unit length of the tube, the solvent's efficiency of reducing *cannabis* will vary because butane evaporates very quickly; the process simply is not capable of controlling how much solvent contacts a given volume of *cannabis* before it evaporates; thus the process is uncontrolled in at least this one way.

Reference [19] Patent Application Publication US 2008/0241339, "Hemp Food Product Base and Processes", by Mitchell et al. Publication Date Oct. 2, 2008. The reference heats hemp seeds in water and then mills or grinds the seeds, the seeds are then added into soups, beverages, and foods; the seeds are reported to have no $\Delta^9$-THC or medicinal *cannabis*.

Recently, with the legalization of medical *cannabis* in 14 states, various edible *cannabis* products have become available; such products include cookies, biscuits, cooking oil, and dairy butter. These products are made without scientific controls by small producers because pharmaceutical companies do not produce edible *cannabis* products. Products like cookies or biscuits are eaten as is; products like cooling oil or dairy butter are usually added or cooked into other foods. Each one of these individual edible products have limitations the most significant one is uncontrolled dosage, cookies or biscuits contain *cannabis* fiber that often makes them green in color, and dairy products such as dairy butter spoil at room temperature.

A process for the production of a food grade intermediate product containing a known amount of medicinal *cannabis* is in controlled ways is the focus of the invention disclosed below.

SUMMARY OF THE INVENTION

The invention relates to the controlled decarboxylation of raw *cannabis*. First by mixing a proportional amount of a cofactor with pulverized dried raw *cannabis*, a solvent (preferably a non-toxic solvent like ethanol) are mixed. Then edible oil is added to the mixture. Then solvent and water are boiled out of the mixture without vaporizing the medicinal *cannabis*. The process provides controlled decarboxylation of raw *cannabis* into medicinal *cannabis*, then bonds medicinal substances contained within *cannabis* to a lipid.

DETAILED DESCRIPTION OF THE INVENTION

Provisional Patent Application No. 61/401,824 Medicinal *Cannabis* in a Fatty Foodstuff filed Aug. 19, 2010 is hereby incorporated by reference into the application.

The invention relates to the controlled decarboxylation of raw *cannabis*. First by mixing a proportional amount of a cofactor with pulverized dried raw *cannabis*, a solvent (preferably a non-toxic solvent like ethanol) are mixed. Then edible oil is added to the mixture. Then solvent and water are boiled out of the mixture without vaporizing the medicinal *cannabis*.

The process provides controlled decarboxylation of raw *cannabis* into medicinal *cannabis*, then bonds medicinal substances contained within *cannabis* to a lipid. The term "medicinal *cannabis*" will be used in this disclosure to refer to decarboxylated raw *cannabis* as a general term for $\Delta$9-THC that may also contain related substances that include, yet are not limited to cannabinoids, cannabiniols, cannbidiols, and cannabigerol. $\Delta$9-THC contained or used in products or processes consistent with this invention may also contain related substances that include, yet are not limited to cannabinoids, cannabiniols, cannbidiols, and cannabigerol.

Furthermore concentrations of $\Delta$9-THC correlate the invention with other medicinal *cannabis* products; such products typically specify concentrations of $\Delta$9-THC; where concentrations of related substances that include yet are not limited to cannabinoids, cannabiniols, cannbidiols, cannabigerol, and other substances are not usually specified in related art.

The Process from Raw *Cannabis*:

A significant aspect of this invention is the transformation of a controlled amount of raw *cannabis* into medicinal *cannabis* consistent with this disclosure. The overall process also bonds the medicinal *cannabis* to a lipid; the lipid is then manufactured into a foodstuff base material containing a controlled amount of medicinal *cannabis* per unit volume of the foodstuff base material.

The making of "medicinal *cannabis*" where the controlled decarboxylation of raw *cannabis* transforms THC acid (THCA-A) into $\Delta$9-THC ($\Delta^9$-THC), as mentioned above, other decarboxylated substances from raw *cannabis* that include cannabinoids, cannabiniols, cannbidiols, and cannabigerol will also be transformed from their acidic counterparts. Since the amount of THC acid that is converted into $\Delta^9$-THC is a primary reference point for comparisons to related art, some discussions will specifically address this transformation, in other discussions the term medicinal *cannabis* will be used.

This is a controlled unique process unique to this invention:

The process begins with the controlled decarboxylation of raw *cannabis* plant material, the plant material is dried at a temperature of 220° F. (104° C.) for 20 minutes.

Once the raw plant material has been dried it is "pulverized" into small pieces it is placed into a pan or container; for sake of this disclosure the term pulverized raw *cannabis* may refer to processes such as crushing, smashing, grinding, or equivalent process.

A specific amount of a cofactor, a consumable hydrocarbon such as Vitamin B6 (Pyridoxine), or Limonene and a mild polar solvent such as a high proof alcohol, preferably ethanol are mixed with the crushed plant material and heated, at an appropriate time a measured volume of edible oil such as hemp oil, or other compatible oil is added to the mixture. Note: alcohol infused vanilla extract may be used as an alcohol with flavor.

The mild polar solvent, preferably ethyl alcohol and water are then evaporated out of the mixture. At sea level alcohol evaporates at a temperature of 173° F. (78.33° C.), and water evaporates at a temperature of 212° F. (100° C.). As heated the mixture will first reach a temperature near 173° F. (78.33° C.) and dwell there until the alcohol is evaporated, the temperature of the mixture will then increase to near 212° F. (100° C.) and dwell there as water the water is evaporated out of the mixture. During this part of the process a specific amount of cofactor (Vitamin B6, Limonene, or other appropriate cofactor) causes the various acidic substances contained within raw cannabis plant material to be converted to medicinal cannabis.

The mild polar solvent wets the raw crushed cannabis and cofactor material allowing them to come into close proximity with each other, the amount of cofactor present controls the chemical activity. The amount of decarboxylation is proportional to the molar mass of cofactor used.

Reduce the amount of cofactor and less decarboxylation will occur in the reaction. Increase the amount of cofactor and more decarboxylation will occur in the reaction until all available THC acid, and other associated acidic compounds are converted into medicinal cannabis. Thus a controlled amount of THCA-A will be converted into Δ9-THC for a given amount of cofactor; adding more cofactor to the mixture will cause more of the THCA-A to be converted into Δ9-THC. The cofactor acts as a normalizing agent for the decarboxylation reaction; it controls the amount of Δ9-THC formed by the decarboxylation reaction. The preferred mild polar solvent is ethyl alcohol.

THCA-A content variations of 5% to 25% by volume are typical in raw cannabis and variations from 10% to 20% are common. A specific amount of cofactor combined with a specific amount of raw cannabis will cause a specific amount of THCA-A to be converted into Δ9-THC. This is true despite the percentage of THCA-A found originally in the raw cannabis material; given an input of 100 grams of raw cannabis the same amount of Δ9-THC will be formed by this decarboxylation process when 25% THCA-A cannabis is used or when 15% THCA-A cannabis is used; the amount of cofactor present limits or truncates the reaction. The amount of reaction is related to the molecular mass of the cofactor, even when additional THCA-A is available for reaction without additional cofactor the reaction will not transform all of the available THCA-A into Δ9-THC. In this instance some of the THCA-A contained within the raw cannabis will simply not be converted to Δ9-THC; the advantage of this approach is that the process will produce essentially the same output even when the THCA-A content of the raw cannabis material input into the process varies; later food production processes could proceed and yield repeatable results with little of no testing of Δ9-THC concentrations.

Other associated substances including yet not limited to cannabinoids, cannabiniols, and cannbidiols may also be transferred in this way.

EXAMPLE 1

Part 1 The Controlled Decarboxylation of Raw Cannabis

Given 100 grams of raw cannabis, it is first dried at a temperature of 250° F. (121.11° C.) for 20 minutes. The dried raw cannabis is then pulverized into small pieces.

The pulverized raw cannabis is placed in a container and mixed with the cofactor Vitamin B6 and solvent ethyl alcohol. The amount of cofactor used depends on the amount of decarboxylation desired. Y, the amount of available THCA-A, depends upon the amount of raw cannabis and its potency (% THCA-A). X, the amount of cofactor required, depends on the THCA-A potency, the molar mass of cofactor (169.2 for vitamin B6) and the molar mass of $\Delta^9$-THC (358.47):

$Y$=(mass of raw cannabis*raw cannabis potency)

$X$=$Y$*(cofactor molar mass/$\Delta^9$-THC molar mass)

For example, 100 g of raw cannabis with potency of 20% THCA-A could provide up to 20 g of $\Delta^9$-THC by reacting with 9.4 g of cofactor B6.

$Y$=(100 g raw cannabis*20% raw cannabis THCA-A potency)=20 g THCA-A $X$=(20 g THCA-A)*(169.2 B6 cofactor molar mass/ 358.47 THCA-A molar mass)=9.4 g of B6 cofactor A 7 g mass of cofactor B6 would partially decarboxylate the THCA-A into 15 g of $\Delta^9$-THC. The 7 g of B6 cofactor limits the reaction and could decarboxylate only 75% of the available THCA-A.

Alternatively, the same 7 g mass of cofactor B6 could fully decarboxylate raw cannabis with a potency of 15%. In fact, the 7 g of cofactor B6, when reacted with 100 g raw cannabis having a potency of greater than 15%, will limit decarboxylation to exactly 15 g of $\Delta^9$-THC.

The mixture is then heated evaporating alcohol and water from the mixture, using the controlled process described above; evaporation takes about 10 minutes. An edible oil is added to the mixture the prior to continued heating of the mixture. The oil may be added prior to evaporation of alcohol an water from the mixture. The oil may also be pre-treated, heated to evaporate water from the oil sometime before being added to the mixture.

In the instance where enough cofactor to convert all, or most of the available THCA-A contained in the raw cannabis material into Δ9-THC the amount of Δ9-THC in the sample will be measured and noted after the decarboxylation reaction has occurred. Subsequent processes can be adjusted to produce more food product when a strong batch (higher percentage THCA-A) of raw cannabis is used and the amount of food product would be reduced when a weaker batch (lower percentage of THCA-A) of raw cannabis is used. The advantage of this approach is that more THCA-A will be converted into Δ9-THC per unit measure of input material, increased efficiency, yet comes with the cost of testing of the potency for each batch, and the adjustment of subsequent food production processes to yield a consistent concentration of Δ9-THC per unit measure in the foodstuffs produced.

Bonding Δ9-THC $\Delta^9$-THC and/or associated compounds to a lipid:

The mixture including an edible oil is then heated to a temperature near the boiling temperature of the $\Delta^9$-THC (314.6° F. at 1 atmosphere, 157° C.), yet below the vaporization temperature of the $\Delta^9$-THC. At 350° F. (176.67° C.) at 1 atmosphere $\Delta^9$-THC will vaporize and be lost in an open or ventilated environment.

Vegetable oils break down at various temperatures, for example; hemp seed oil begins to break down at 330° F. (165.56° C.), coconut oil at 350° F., and olive oil at 375° F.

The optimal temperature range for bonding the $\Delta^9$-THC and associated substances to hemp seed oil in an open environment is near the near the boiling temperature of the $\Delta^9$-THC; temperatures used may be adjusted to change the ratio of $\Delta^9$-THC to cannabinol or other *cannabis* related substances.

An essential concept is to heat *cannabis* related materials near their boiling point in the presence of an oil bonding the substances together. Controlling loss by vaporization and conversion into other *cannabis* related substances by controlling temperature is also an aspect of the invention.

The boiling of both the $\Delta^9$-THC in the hot oil provides an environment where the $\Delta^9$-THC and edible oil are free to associate; the substances chemically bond to each other readily in this environment; this process bonds the $\Delta^9$-THC to a lipid forming "Δ9-THC-lipid" in a controlled way, this is a unique aspect of the invention. The process not only incorporates $\Delta^9$-THC, it also incorporates associated substances, including, yet not limited to cannabinoids, cannabiniols, and cannbidiols in controlled ways.

Applicant notes that boiling points, and vaporization temperatures of materials used in this invention vary with ambient pressure and that specific temperatures referenced may vary upon ambient pressure; critical temperatures may therefore vary based on environmental pressures that can vary based on elevation, pressurized environments or even contaminants.

EXAMPLE 1

Part 2: Forming a Δ9-THC-Lipid

Add 500 mL of hemp seed oil to the mixture and heat following the constraints described above for 15 minutes.

The material is then cooled to a temperature where it can be rendered into a fatty foodstuff base material. The material may be filtered or strained at this point in the process.

The controlled decarboxylation of raw *cannabis* is a unique aspect of this invention. Other unique aspects are the combinations of materials and temperatures used. No toxic substances are used in the best mode of this invention: preferred materials include raw *cannabis*, Vitamin B6, ethyl alcohol, and hemp seed oil; even so other similar materials and slight modifications to processes described above that are obvious to a person of ordinary skill in the art are considered an embodiment of the invention described herein.

One instance of such a process is were a intermediate products is bonded to a lipid using some of the same steps described above; here the intermediate product is mixed with an oil, preferably hemp oil, and heated to a temperature above the boiling temperature of the $\Delta^9$-THC (314.6° F. or 157° C. at sea level), at or above the boiling temperature of the oil used in the mixture, yet below the vaporization temperature of the $\Delta^9$-THC (350° F. or 176.67° C. at sea level) and below the vaporization temperature of the oil. The mixture may then be added to a foodstuff. In this instance the purity and quantity of the medicinal intermediate product used will typically be known, testing and measuring the sample may be used as control mechanism. Alternatively the final product itself may be tested and measured to determine the medicinal content per unit volume of the product.

Medicinal foodstuff base materials consistent with this invention may be processed into other various final products through standard processes for making chocolate, suppositories, rubs, salves, or other final products as long as processing temperatures do not exceed the vaporization and boiling temperature of $\Delta^9$-THC. Chocolate chip cookies, for example may be made using chocolate chips made from medicinal foodstuff base materials and be baked into cookies in a oven operating at temperatures below the boiling temperature of medicinal *cannabis*, 315 degrees F. boiling temperature is preferred, these processes must be kept below the vaporization temperature of 350° F. (176.67° C.) at sea level.

BRIEF DESCRIPTION OF THE DRAWINGS

FIG. 1 shows Basic Cannabinoid Structures:

THCA-A (THC acid), Decarboxylation is the loss of $CO_2$ from a molecular structure; when THCA-A decarboxylates the psychoactive substance $\Delta^9$-THC is formed; $\Delta^9$-THC is depicted in FIG. 1.

CBN (cannabiniol) is also depicted; CBN is formed by degeneration of $\Delta^9$-THC.

CBDA (cannabidiolic acid) and CBD (cannabidiol) are also depicted in FIG. 1. When CBDA is decarboxylated CBD is formed.

Since CBD may be transformed into $\Delta^9$-THC, FIG. 1 also depicts that this Transformation relates to a small change in chemical structure.

Notes regarding the chemical formula and molecular weight of depicted cannabinoid structures:

CBD and $\Delta^9$-THC have the identical Chemical Formula $C_{21} H_{30} O_2$; & Molecular Weight 314.5.

CBDA has a Chemical Formula $C_{22} H_{30} O_4$; Molecular Weight 358.5.

CBN has a Chemical Formula $C_{21} H_{26} O_2$; Molecular Weight 310.4.

FIG. 2: shows The Controlled Decarboxylation Process:

FIG. 2 shows a series of steps of the controlled decarboxylation process. First raw *cannabis* is dried, the second step is to pulverize then the dry raw *cannabis*, the third step shown is to mix pulverized dried raw *cannabis* with cofactor and solvent. This third step decarboxylates the medicinal *cannabis* in a controlled way through a chemical reaction proportional to the amount of cofactor used.

The fourth step in FIG. 2 is adding an oil (lipid in liquid state) to the mixture. In the fifth step, the mixture is heated while observing critical temperatures. The sixth step is evaporating the solvent (ethyl alcohol evaporates at 174 degrees F.). The seventh step evaporating any water from the mixture (water evaporates at 212 degrees F.). The eighth step bond medicinal *cannabis* to a lipid is where the mixture is heated near the boiling temperature of medicinal *cannabis* 314.6 degrees F. forming a Medicinal *Cannabis* Lipid. The ninth step is cooling the mixture. The tenth step straining out the particulates. The final step shown in FIG. 2 is placing the mixture in a container.

REFERENCES

[1] Journal of Chromatography 8,877 (2009) 4115-4124: "Innovative development and validation of an HPLC/DAD method for the qualitative determination of major cannabinoids in *cannabis* plant material": Benjamin De Backer et al.

[2] U.S. Pat. No. 6,365,416 B1: "Method of Preparing Δ9-THC", Elsohly et al. publication date Oct. 26, 1998.

[3] U.S. Pat. No. 6,730,519: "Method of Preparing Δ9-THC", Elsohly et al. publication date Jul. 4, 2002.

[4] Patent Application Publication US 2002/0039795 A1 "Method of Preparing Δ9-THC", Elsohly et al. patent date Apr. 2, 2002; filing date Oct. 26, 1998.

[5] U.S. Pat. No. 7,524,881 B2: "Production of Δ9-THC", Goodwin et al. patent date Apr. 28, 2009.

[6] U.S. Pat. No. 7,592,468 B2: "Production of Δ9-THC", Goodwin et al. patent date Sep. 22, 2009.
[7] GW pharmaceuticals of Great Britain Misc. reports on their website July 2010.
[8] "Effects of canabidiol on schizophrenia-like symptoms in people who use *cannabis*"; from The British Journal of Psychiatry (2008)
[9] Therapeutic Potential of Non-Psychotropic Cannabidiol in Ischemic Stroke; Hayakawa, Mishima, & Fujiwara; Dept. of Neuropharmacology, Faculty of Pharmaceutical Sciences, Fukuoka University, Published Jul. 8, 2010. $\Delta^9$-THC
[10] "Isolation of $\Delta^9$-THCA-A from hemp and analytical aspects concerning the determination of $\Delta^9$-THC in *cannabis* products"; Dussy, et al. Institute of Legal Medicine, Basel Switzerland, available online Aug. 18, 2004.
[11] Wikipedia "Cannabinoid" webpage, August 2010.
[12] *Cannabis* and *Cannabis* Extracts: Greater Than the sum of Their Parts?, by John M. McPartland and Ethan B. Russo; 2001 The Haworth Press, Inc.
[13] U.S. Pat. No. 7,674,922 "Process the Production of Delta-9-Tegrahdrocannabinol", Burdick et al. Granted Mar. 9, 2010
[14] www.*Cannabis*-Science.com August 2010, The drawing entitled "Cannabinoids"
[15] Patent Application Publication US 2008/0221339 by Webster et al. published Sep. 11, 2008.
[16] Hemp Husbandry, an excerpt from Chapter 6 Cannabinoid Chemistry: Robert A. Nelson, Copyright 2000
[17] "How to Make Hash oil From Marijuana", author unknown, found on the internet July 2010.
[18] "How to Make Wicked Hash" by Lisa Scammel and Bianca Sind, written Wednesday May 22, 2002; found on www.cannabisculture.com in July 2010.
[19] Patent Application Publication US 2008/0241339, "Hemp Food Product Base and Processes", by Mitchell et al. Publication Date Oct. 2, 2008.

The invention claimed is:

1. A process for controlling a decarboxylation of acidic cannabinoids, comprising:
   a) performing controlled drying of a raw *cannabis* base material at a temperature less than the boiling point of temperature of Δ-9-tetrahydrocannabinol;
   b) pulverizing the dried raw *cannabis* into small pieces;
   c) mixing the ground dried raw *cannabis* with a cofactor vitamin B6 and a solvent to form a mixture,
   wherein an amount of the cofactor vitamin B6 depends on the degree of the decarboxylation of the acidic cannabinoids.

2. The process of claim 1, further comprising adding an oil to the mixture.

3. The process of claim 1, further comprising heating the mixture and evaporating the solvent from the mixture.

4. The process of claim 3, wherein the solvent is alcohol and/or water.

5. The process of claim 1, wherein the controlled drying of the raw *cannabis* is performed at a temperature not exceeding 250° F.

* * * * *